US008199644B2

(12) United States Patent (10) Patent No.: US 8,199,644 B2
Carmichael et al. (45) Date of Patent: Jun. 12, 2012

(54) SYSTEMS AND METHODS FOR PROCESSING ACCESS CONTROL LISTS (ACLS) IN NETWORK SWITCHES USING REGULAR EXPRESSION MATCHING LOGIC

(75) Inventors: Jeff Carmichael, Poway, CA (US); Gary Smerdon, Saratoga, CA (US)

(73) Assignee: LSI Corporation, Milpitas, CA (US)

( * ) Notice: Subject to any disclaimer, the term of this patent is extended or adjusted under 35 U.S.C. 154(b) by 3 days.

(21) Appl. No.: 12/774,024

(22) Filed: May 5, 2010

(65) Prior Publication Data

US 2010/0217936 A1    Aug. 26, 2010

Related U.S. Application Data

(62) Division of application No. 11/845,696, filed on Aug. 27, 2007.

(60) Provisional application No. 60/888,003, filed on Feb. 2, 2007.

(51) Int. Cl.
| | |
|---|---|
| *G01R 31/08* | (2006.01) |
| *G06F 11/08* | (2006.01) |
| *G08C 15/00* | (2006.01) |
| *H04J 1/16* | (2006.01) |
| *H04J 3/14* | (2006.01) |
| *H04L 1/00* | (2006.01) |
| *H04L 12/26* | (2006.01) |

(52) U.S. Cl. ......... 370/230; 370/235; 711/118; 711/154
(58) Field of Classification Search .................. 370/230, 370/235, 389, 392; 710/36, 51, 240; 711/118, 711/154; 726/26
See application file for complete search history.

(56) References Cited

U.S. PATENT DOCUMENTS

| | | | | |
|---|---|---|---|---|
| 5,475,829 | A | * | 12/1995 | Thome ........................... 711/152 |
| 6,023,760 | A | * | 2/2000 | Karttunen ...................... 712/300 |
| 6,314,431 | B1 | * | 11/2001 | Gornish ......................... 712/205 |
| 6,484,239 | B1 | * | 11/2002 | Hill et al. ........................ 711/137 |
| 6,643,260 | B1 | | 11/2003 | Kloth et al. |
| 6,651,096 | B1 | * | 11/2003 | Gai et al. ........................ 709/223 |
| 6,658,002 | B1 | | 12/2003 | Ross et al. |
| 6,658,458 | B1 | | 12/2003 | Gai et al. |
| 6,715,029 | B1 | | 3/2004 | Trainin et al. |
| 6,775,737 | B1 | | 8/2004 | Warkhede et al. |
| 6,798,746 | B1 | | 9/2004 | Kloth et al. |
| 6,867,991 | B1 | | 3/2005 | Tezcan et al. |
| 6,868,065 | B1 | | 3/2005 | Kloth et al. |
| 6,870,812 | B1 | | 3/2005 | Kloth et al. |
| 6,871,265 | B1 | | 3/2005 | Oren et al. |
| 6,874,016 | B1 | | 3/2005 | Gai et al. |
| 6,957,215 | B2 | * | 10/2005 | Stark ...................................... 1/1 |

(Continued)

OTHER PUBLICATIONS

International Search Report for PCT/US2008/051574, filed Jan. 21, 2008.

(Continued)

*Primary Examiner* — Kwang B Yao
*Assistant Examiner* — Benjamin H Elliott, IV

(57) ABSTRACT

A network node, such as an Ethernet switch, is configured to monitor packet traffic using regular expressions corresponding to Access Control List (ACL) rules. In one embodiment, the regular expressions are expressed in the form of a state machine. In one embodiment, as packets are passed through the network node, an access control module accesses the packets and traverses the state machine according to certain qualification content of the packets in order to determine if respective packets should be permitted to pass through the network switch.

7 Claims, 11 Drawing Sheets

U.S. PATENT DOCUMENTS

| | | |
|---|---|---|
| 6,970,971 B1 | 11/2005 | Warkhede et al. |
| 6,980,552 B1 | 12/2005 | Belz et al. |
| 7,002,965 B1 | 2/2006 | Cheriton |
| 7,028,098 B2 * | 4/2006 | Mate et al. ............... 709/238 |
| 7,028,136 B1 | 4/2006 | Priyadarshan et al. |
| 7,043,494 B1 | 5/2006 | Joshi et al. |
| 7,051,078 B1 * | 5/2006 | Cheriton ................. 709/214 |
| 7,065,083 B1 | 6/2006 | Oren et al. |
| 7,065,609 B2 | 6/2006 | Eatherton et al. |
| 7,080,195 B2 | 7/2006 | Ngai et al. |
| 7,082,492 B2 | 7/2006 | Pullela et al. |
| 7,093,092 B2 | 8/2006 | Stojancic |
| 7,103,708 B2 | 9/2006 | Eatherton et al. |
| 7,120,627 B1 * | 10/2006 | Schabes et al. ................. 1/1 |
| 7,133,914 B1 | 11/2006 | Holbrook |
| 7,162,486 B2 * | 1/2007 | Patel et al. ..................... 1/1 |
| 7,171,525 B1 * | 1/2007 | Norman et al. ............ 711/150 |
| 7,184,985 B2 * | 2/2007 | DeTreville ................. 705/51 |
| 7,411,953 B2 * | 8/2008 | Monette et al. ............ 370/389 |
| 7,472,262 B2 * | 12/2008 | Sun ............................ 712/237 |
| 7,627,742 B2 * | 12/2009 | Bose et al. ................. 712/220 |
| 2002/0073301 A1 * | 6/2002 | Kahle et al. ............... 712/235 |
| 2003/0195943 A1 * | 10/2003 | Bradshaw et al. .......... 709/217 |
| 2004/0193856 A1 * | 9/2004 | Wang et al. ................ 712/238 |
| 2004/0210749 A1 * | 10/2004 | Biles ........................... 712/240 |
| 2004/0268085 A1 * | 12/2004 | Hara et al. .................. 711/213 |
| 2005/0154867 A1 * | 7/2005 | DeWitt et al. .............. 712/239 |
| 2005/0195840 A1 * | 9/2005 | Krapp et al. ............... 370/401 |
| 2006/0101195 A1 * | 5/2006 | Jain ............................ 711/104 |
| 2006/0242394 A1 * | 10/2006 | Uchiyama ................... 712/241 |
| 2007/0174599 A1 * | 7/2007 | Dowling ..................... 712/239 |
| 2007/0186049 A1 * | 8/2007 | Luick .......................... 711/137 |
| 2009/0052451 A1 * | 2/2009 | Etheridge ................... 370/392 |
| 2009/0303990 A1 * | 12/2009 | Ambrose et al. ........... 370/389 |
| 2010/0217936 A1 * | 8/2010 | Carmichael et al. ........ 711/118 |

OTHER PUBLICATIONS

Written Opinion for PCT/US2008/051574, filed Jan. 21, 2008.

Brodie, et al. "A Scalable Architecture for High-Throughput Regular-Expression Pattern Matching," The Computer Society, 33$^{rd}$ International Symposium on Computer Architecture, pp. 191-202, Boston, MA, Jun. 2006.

* cited by examiner

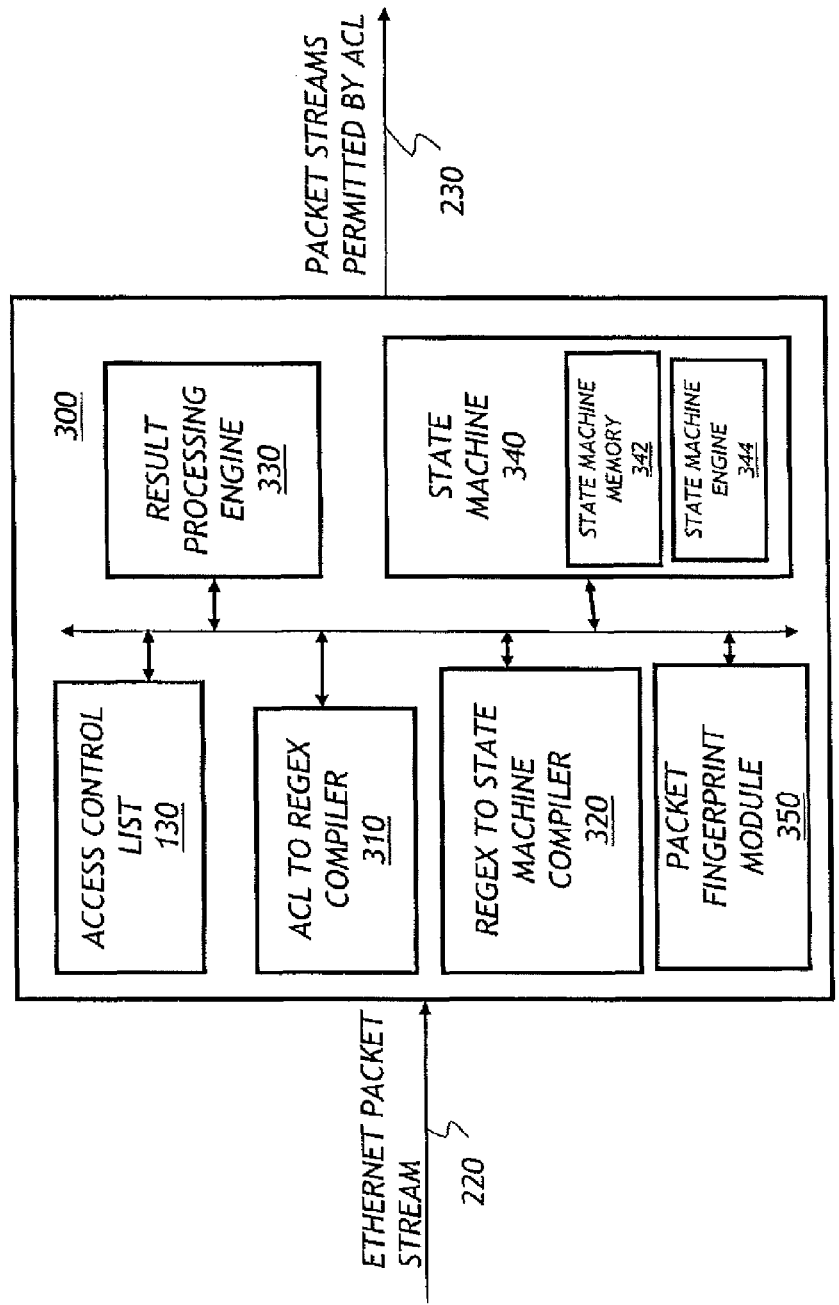

Permit Output Processing Logic:

```
result=1 // default to permit
If (num_results) {
    result=results[num_result]
    While (--num_results ) {
        if (results[num_result] < result) result = results[num_results]
    }
}
If (result && 1) permit
Else deny
```

| Input Data | | Match Result Code | Action |
|---|---|---|---|
| Source MAC | 000012afb983 | 0021 | Permit |
| Source IP | 0a0a030c | 0030 | |
| Source Port | 2383 | | |
| Dest MAC | 000012afb312 | | |
| Dest IP | 0a0a0202 | | |
| Dest Port | 80 | | |
| Protocol | 80 | | |
| Source MAC | 000012afb983 | 0041 | Permit |
| Source IP | 0a0a010c | | |
| Source Port | 2383 | | |
| Dest MAC | 000012afb312 | | |
| Dest IP | 0a0a0202 | | |
| Dest Port | 80 | | |
| Protocol | 80 | | |

FIGURE 7

SYSTEMS AND METHODS FOR PROCESSING ACCESS CONTROL LISTS (ACLS) IN NETWORK SWITCHES USING REGULAR EXPRESSION MATCHING LOGIC

CROSS-REFERENCE TO RELATED APPLICATIONS

This is a divisional of U.S. patent application Ser. No. 11/845,696, filed on Aug. 27, 2007, the disclosure thereof being incorporated herein by reference.

This application claims the benefit of U.S. Provisional Application No. 60/888,003, filed Feb. 2, 2007, which is hereby incorporated by reference in its entirety herein.

BACKGROUND OF THE INVENTION

1. Field of the Invention

The invention relates to systems and methods for processing Access Control Lists (ACLs) used in network communications, such as in Ethernet switches, using regular expression matching logic.

2. Description of the Related Art

ACLs are commonly used in Ethernet switching devices to control the flow of packet traffic through the switching devices in order to protect networks from unauthorized access, for example. An ACL typically determines whether or not a packet should be allowed to pass through the switch and on to one or more computing device that are in communication with the switch. An ACL typically includes a list of rules, where each rules comprises a qualification pattern indicating one or more attributes of packets, and an action corresponding to each qualification pattern that is performed if the qualification pattern is matched by a packet. Portions of the packet, such as information in the packet headers, is compared to the qualification patterns in order to determine if the packet data, referred to herein as the packet's qualification content, matches the qualification patterns of the ACL. If a qualification pattern of the ACL matches the packet's qualification content, an action associated with the qualification pattern is executed. The qualification patterns and qualification content may comprise various components of packets, such as IP and TCP headers, including a combination of Ethernet frame (MAC) fields, Internet Protocol (IP) addresses and Transmission Control Protocol (TCP) port and protocol information. One or more components of a packet's 7-tuple, which comprises a source MAC address, destination MAC address, source IP address, destination IP address, source TCP port, destination TCP port and protocol, may be considered by qualification patterns in an ACL. In order to control flow of packets, each qualification pattern of the ACL is associated with one or more actions that are executed in response to fulfillment of the rule. An action may be to allow a packet to flow through the switch or to deny the packet from flowing through the switch.

Switching implementations typically use a ternary match methodology to establish an "exact match" of a packet's qualification content on the ACL qualification patterns in order to execute the associated actions, e.g., permit or deny passage of the packet. ACL qualification patterns may be specified as ternary exact matches on the packets ACL qualification content, such as the 7-tuple. U.S. Pat. No. 6,651,096 titled "Method and apparatus for organizing, storing and evaluating access control lists," which is hereby incorporated by reference in its entirety, describes ACL's wherein each field represents a specific address, range of addresses or "don't care" value. Some examples of ACLs are:

| | Qualification pattern | Action |
|---|---|---|
| 1 | source_mac = 00:00:12:f8:03:23 | Permit |
| 2 | source_IP = 10.10.3.0/24 destination_IP = 10.10.0.0/16 | Permit |
| 3 | destination_IP = 10.10.2.0/24 | Deny |
| 4 | source_IP = 10.10.1.0/24 | Permit |

Implementation of such an ACL is executed in order until the first definitive qualification pattern is matched by a packet's qualification content. For example, with the above ACL a packet with the 7-tuple:

Source_mac=00:00:12:af:b9:83
Destination_mac=00:00:12:af:b3:12
Source_IP=10.10.3.12
Destination_IP=10.10.2.2
Source_Port=2383
Destination_Port=80
Protocol=http would not be affected by rule 1 (the source_mac is different than the source_mac in qualification pattern 1), but would be permitted by rule 2 (the source_IP and the destination_IP of the packet's qualification content match the source_IP and destination_IP of qualification pattern 2). However the 7-tuple:

Source_mac=00:00:12:af:b9:83
Dest_mac=00:00:12:af:b3:12
Source_ID=10.10.1.12
Dest_IP=10.10.2.2
Source_Port=2383
Dest_Port=80
Protocol=http would match qualification pattern 3, and thus be denied passage through the Ethernet switch. More particularly, the qualification content, e.g., the packet's 7-tuple, does not match qualification pattern 1 because the source_MAC of the packet is different than that specified in qualification pattern 1; the packet does not match qualification pattern 2 because the source_IP of the packet does not match the source_IP range of qualification pattern 2. However, with the subnet mask "/24" of qualification pattern 3, e.g., indicating that only the first 24 bits of the 32 bit IP address are to be considered by the qualification pattern, the destination_IP of 10.10.2.2 satisfies qualification pattern 3.

ACL rulesets typically evaluate every packet on ingress and/or egress from an Ethernet switch. ACL rule processing has typically been implemented in systems using software processing or Ternary Content Addressable Memories (TCAMs). Since ACLs require a true exact match (with ternary exclusions) and since the majority of packets will match at least one entry, traditional algorithmic acceleration methods (such as hashing) for high-speed match sorting are not effective. Additionally, the silicon area and power required to process an ACL using TCAMs grows linearly (or greater) as the number of rules and depth of search into each packet grows. This limits the number of ACLs that can be configured in a system, restricting the security that can be applied.

SUMMARY

In one embodiment, a method of selectively allowing data packets to flow through a network switch to respective recipients of the data packets comprises receiving an access control list comprising a plurality of qualification patterns each associated with an action, the qualification patterns each indicating one or more packet characteristics, converting the qualification patterns into corresponding regular expressions, generating a state machine comprising a plurality of state transition instructions corresponding to the regular expressions, wherein the state machine comprises a plurality of terminal states corresponding with matches to respective regular expressions, storing the state transition instructions in a memory that is accessible by a network switch, and receiving a plurality of packets. In one embodiment, for each packet received by the network switch, the method further comprises generating a packet fingerprint comprising an indication of one or more of the packet characteristics, and traversing the state machine using the packet fingerprint in order to locate a matched regular expression that is matched by the packet fingerprint and, in response to locating the matched regular expression, executing the action associated with the matched regular expression.

In one embodiment, a method of storing a state machine comprises storing a state machine in a memory, the state machine comprising a plurality of states and transitions therebetween, the state machine comprising a plurality of branches, each having a terminal state, that are associated with matches of an input string to respective regular expressions, selecting a predetermined number of states in each branch of the state machine for storage in a cache memory that has faster access and read times than the memory, selecting one or more additional states of at least a first branch of the state machine in response to determining that the first branch comprises unselected states that are associated with each of a plurality of branches, deselecting one or more states of at least a second branch of the state machine in response to determining that the second branch comprises selected states that are only associated with the second branch, and storing the selected states of the state machine in the cache memory.

In one embodiment, a compiler for generating a plurality of regular expressions corresponding to rules of an access control list, the rules comprising qualification patterns and associated actions, wherein the regular expressions are configured to match packets having qualification content that matches the qualification patterns of the access control list, comprises an input module adapted to receive an access control list, and a conversion module adapted to convert the qualification patterns into regular expressions that locate the respective qualification patterns, the conversion module also adapted to generate match result codes associated with each regular expression, the match result codes indicating priorities of the respective qualification patterns and actions associated with the respective qualification patterns.

In one embodiment, a method of monitoring passage of packets of a packet stream through a network node comprises receiving a plurality of state transition instructions representing a state machine having a plurality of terminal states, receiving a packet of the packet stream, generating a packet fingerprint comprising an ordered representation of characteristics of the packet, the characteristics comprising one or more of a source MAC address, a destination MAC address, a source IP address, a destination IP address, a source TCP port, a destination TCP port, a protocol, and a payload of the packet, traversing the state machine using the bits of the packet fingerprint, selecting one terminal state of the state machine corresponding with a highest priority access control rule, and determining an action associated with the selected terminal state.

In one embodiment, a computerized system for monitoring packets that pass through a network node comprises a memory storing a state machine, the state machine comprising a plurality of states and transitions therebetween, the state machine comprising a plurality of branches, each having a terminal state, that are associated with matches of an input string to respective regular expressions, and means for selecting a subset of the plurality of states that are likely to be most frequently traversed by packets received by the network node.

BRIEF SUMMARY OF THE DRAWINGS

FIG. 3 is a block diagram of one embodiment of modules of an access control module that may be used to control packet flow through a network node.

FIG. 7 illustrates exemplary code that may be executed by the result processing logic in order to select one of multiple match result codes that are output from the state machine.

DETAILED DESCRIPTION OF CERTAIN EMBODIMENTS

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
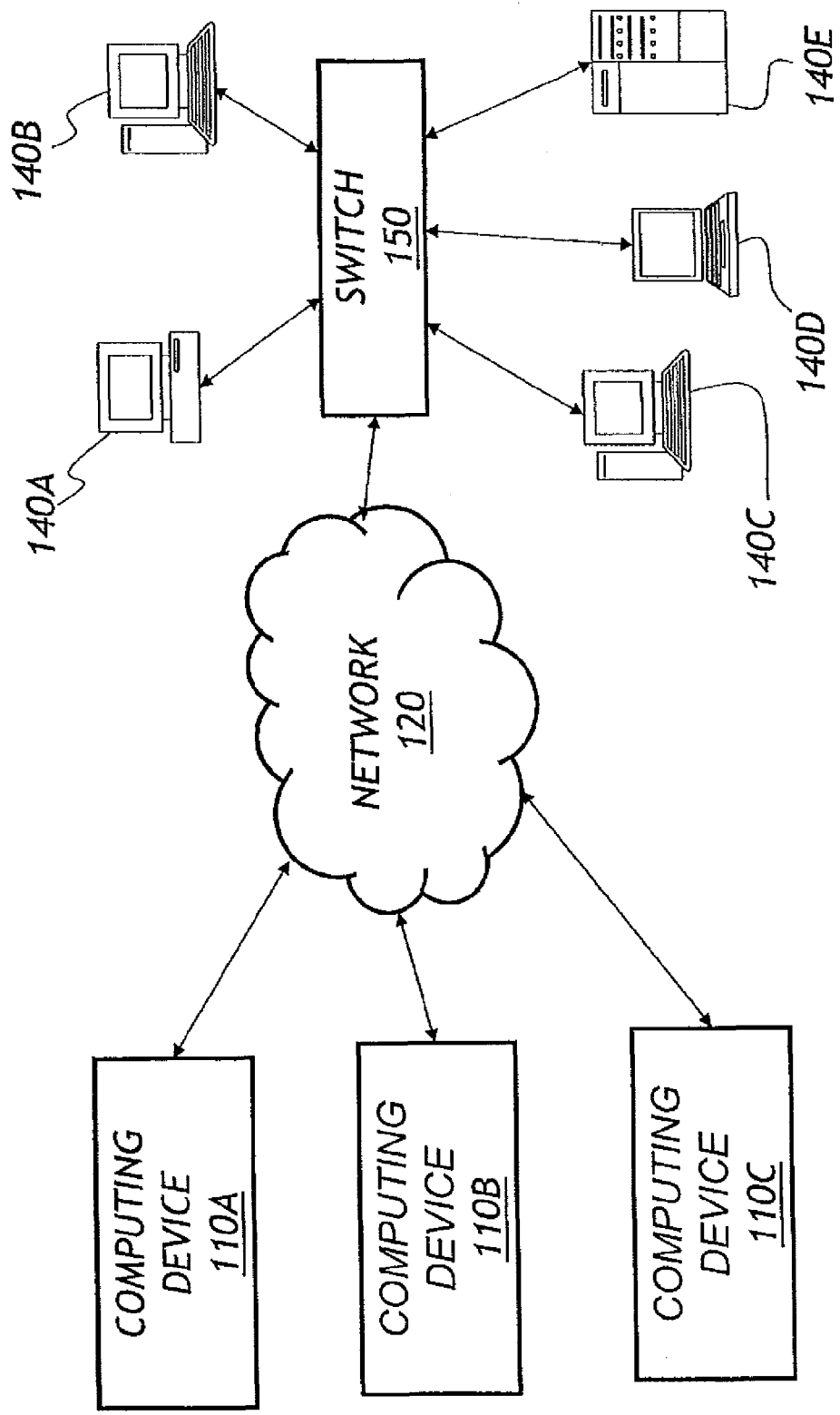
FIG. 1 is a block diagram of one embodiment of a networked computer system.

FIG. 1 is a block diagram of one embodiment of a networked computer system. In the embodiment of FIG. 1, multiple computing devices 110A, 110B, 110C are in communication with a switch 150, such as an Ethernet switch 150, via a network 120. In one embodiment, the network 120 may comprise one or more wired and/or wireless networks, such as one or more LANs, WANs, MANs, and/or the Internet. In the embodiment of FIG. 1, the computing devices 110 may comprise any computing device, such as desktop computer, a laptop computer, a cellphone, a personal digital assistant, a kiosk, an audio player, or any other computing device that communicates with other computer devices. In one embodiment, one or more of the computing devices 110 provide content to other devices that are coupled to the network 120, such as, for example, webpages, multimedia files, and documents.

In the embodiment of FIG. 1, the switch 150 receives all of the packets destined for one or more of the computing devices 140A-140E. The switch 150 is configured to determine a destination for each incoming packet and route the incoming packet to the appropriate destination. In certain embodiments described herein, the switch 150 comprises an ACL that matches qualification content of incoming and/or outgoing packets to qualification patterns of the ACL rules, in order to selectively block unwanted packets from passing through the switch 150. In the embodiment of FIG. 1, computing devices 140A, 140B, and 140C comprise desktop computers, computing device 140D comprises a laptop computer, and computing device 140E comprises a server and/or a server farm. In other embodiments, other computing devices may be in communication with the switch 150, such as portable computing devices, including PDAs and smart phones, for example.

Figure 2:
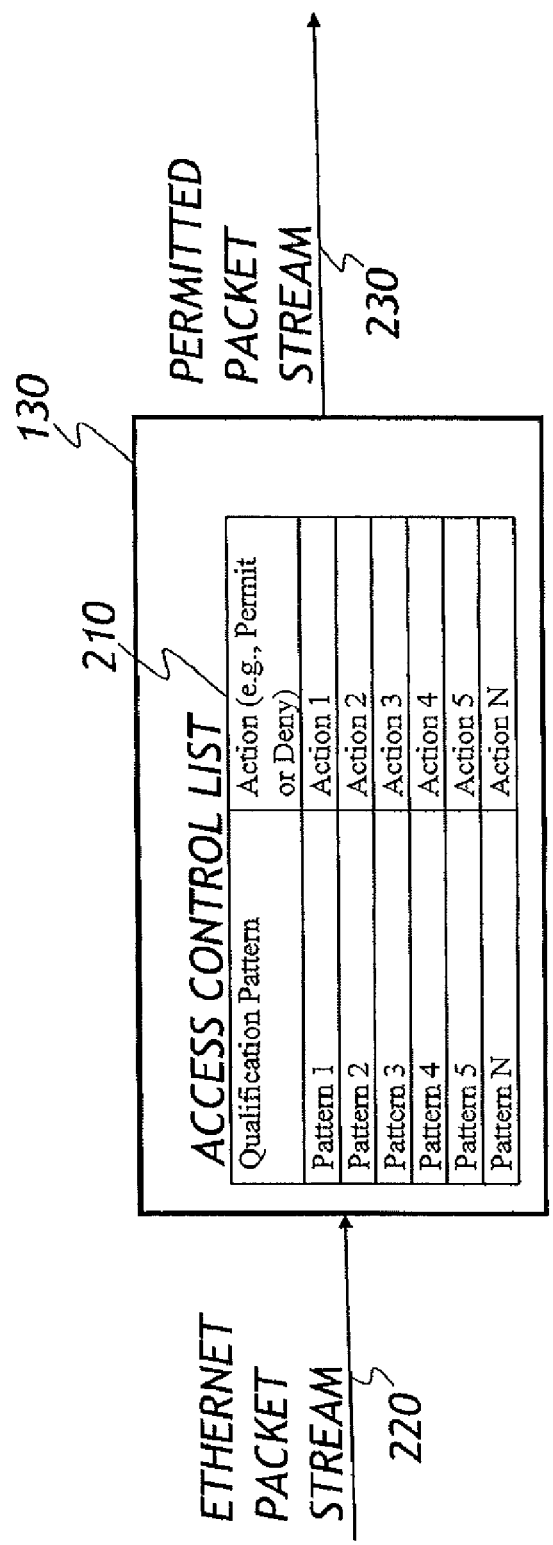
FIG. 2 illustrates one embodiment of the Ethernet switch of FIG. 1, wherein the Ethernet switch accesses an access control list ("ACL") that is configured to control the flow of packets through the switch.

FIG. 2 illustrates one embodiment of the Ethernet switch 150 of FIG. 1, wherein the Ethernet switch comprises an access control list ("ACL") 210 that is configured to monitor the flow of packets through the switch. In one embodiment, the ACL 210 comprises a plurality of qualification patterns comprising attributes of a packet, and actions associated with each of the qualification patterns. For example, a qualification pattern may indicate a certain range of destination IP addresses, or a particular source MAC address. In the embodiment of FIG. 2, the Ethernet switch 150 determines which of the qualification patterns 1-N of the ACL 210 are matched by qualification content of packets in the packet stream 220 and, upon locating a matching packet, performs the action associated with the matched qualification pattern. For example, if qualification pattern 2 specifies a range of source IP addresses, and the associated action 2 indicates that packets within that range of source IP addresses should be denied, a packet that is received from a source IP address within the specified range is denied passage through the Ethernet switch 150. In certain embodiments, multiple qualification patterns may be matched by a packet and additional processing logic may be used to determine which of multiple possible actions should be executed with respect to a particular packet. In FIG. 2, those packets that are permitted to pass through the Ethernet switch are outputted in the permitted packet stream 230. In one embodiment, the permitted packet stream 230 may comprise connections to each of multiple computing devices, such as devices 140A-140E of FIG. 1, wherein the packets are routed to the appropriate destination device 140A-140E.

FIG. 3 is a block diagram of one embodiment of exemplary modules of an access control module that may be used to control packet flow through a network node, such as an Ethernet switch or router, for example. In general, the word module, as used herein, refers to logic embodied in hardware or firmware, or to a collection of software instructions, possibly having entry and exit points, written in a programming language, such as, for example, C or C++. In the embodiment of FIG. 3, the access control module 300 comprises the access control list 130, an ACL to RegEx compiler 310, a RegEx to state machine compiler 320, a result processing engine 330, and a state machine module 340. Each of these modules is discussed in further detail below.

The access control module 300 advantageously converts the ACL 130 into regular expressions that are stored in the form of a state machine. As packets are passed through a network switch, for example, the access control module 300 may access the packets and traverse the state machine according to certain qualification content of the packets in order to determine if respective packets should be permitted to pass through the network switch. In one embodiment, the functionality of the access control module 300 is integrated into a network switch. In other embodiments the access control module 300 may be in communication with the network switch, or other portion of a network. Depending on the embodiment, the access control module 300 may comprise fewer or additional modules than depicted in FIG. 3.

In the exemplary embodiment of FIG. 3, the ACL to RegEx compiler 310 (also referred to herein as the "RegEx compiler 310") accesses the ACL 130 and converts the qualification patterns into a series of regular expressions and associated match result codes that correspond with the ACL actions. In one embodiment, the RegEx compiler 310 initially orders the ACL qualification patterns in an optimal order for compiling to regular expressions. For example, qualification patterns each referring to certain fields of packet qualification content (e.g., fields of a packet 7-tuple) may be listed first on the ACL, such that in an embodiment where an ACL has a small number of rules based on the packet destination fields, but a large number of rules based on the packet source fields, the RegEx compiler may list the qualification patterns that consider one or more source fields early in the ACL. As will be appreciated after considering the description below, ordering of the qualification patterns of the ACL in this manner may increase an efficiency of a state machine that corresponds to the qualification patterns.

In one embodiment, each of the rules of the ACL are compiled into a single regular expression matching the qualification pattern of the rule and a match result code that encodes priority information for the rule and/or the action of the rule. In some embodiments, certain qualification patterns, such as port ranges, for example, may require multiple regular expressions to establish a match, while qualification patterns of other rules may be combined into a single regular expression.

In certain embodiments, the match result codes indicate a priority of the respective result codes, so that when multiple qualification patterns are matched by a packet, the match result codes may be compared in order to determine the highest priority match result code. In addition, in one embodiment the match result codes also include an indication of the action associated with the corresponding qualification pattern. In this embodiment, the match result code indicates both a priority of the match result code, in comparison to other match result codes, and an action associated with each match result code, such as permit or deny. In one embodiment, for example, the match result code may comprise 32 bits, wherein the first 31 bits encode a result processing priority and the last bit encodes the action associated with the corresponding ACL rule, such as permit=1 or deny=0. In this embodiment, the match result codes may be sorted in order to determine a highest priority match result code and the corresponding action may be easily determined from the sorted match result codes. In other embodiments, priority and/or action information may be encoded in various other manners in match result codes.

The regular expressions generated by the RegEx compiler 310 advantageously match portions of the qualifying content of a packet that are located in a know position of a packet fingerprint. The term "packet fingerprint," as used herein, describes a data structure comprising information regarding a packet, such as information from a packet header and/or payload of the packet, wherein the information is compiled into a known sequence. In certain embodiments, the locations of packet fields may be determined by analyzing the surrounding packet data. For example, "options" flags may be present in an IP packet header, which change the location of the TCP header.

Figure 3A:
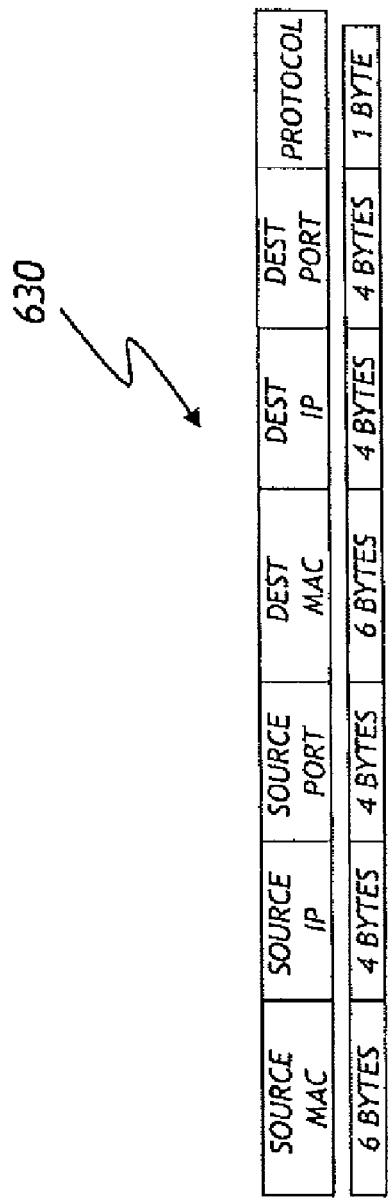
FIG. 3A illustrates exemplary packet attributes that may be included in a packet fingerprint.

FIG. 3A illustrates an exemplary packet fingerprint comprising information regarding each attribute of a packet's 7-tuple in a known sequence, and with a defined size for each attribute. Thus, the RegEx compiler 310 generates the regular expressions so that only those portions of the packet fingerprints that are associated with attributes included in qualification patterns are accessed when the regular expression is evaluated. For example, if a packet fingerprint comprises 10 bytes, including 6 bytes for a source MAC address followed by 4 bytes for a source IP address, a qualification pattern that only looks at the source IP address of packets would not need to look at the first 6 bytes of the packet's fingerprint (or would match any characters in the first 6 bytes to a wildcard expression). Thus, the regular expression associated with such a qualification pattern may include a wildcard operator that matches any characters in the first 6 bytes of each packet fingerprint (e.g., "{6}") when evaluating that regular expression. Wildcard operators may also be used in the generated regular expressions to quickly match portions of the packet fingerprint that are irrelevant due to a subnet or port range indicated in the qualification pattern. For example, a regular expression for a qualification pattern including the suffix "/24", indicating that only the first 24 bits of a 32 bit IP address are to be considered by the qualification pattern, may include a wildcard that matches any characters in the first 24 bits of the IP address.

In certain embodiments, the RegEx compiler 310 orders the fields of the qualification patterns in a predetermined order for compiling to regular expressions and then converts the regular expressions to one or more state machines. In one embodiment, the order of the qualification pattern fields may be adjusted based on characteristics of the state machine. In embodiments where the order of the qualification pattern fields may be adjusted, the size and/or speed of evaluating packets may be improved as the most frequently accessed fields of the qualification patterns may be evaluated by earlier portions of the state machine.

In one embodiment, the order of the qualification pattern fields depends on the size of the cache (e.g., SRAM 820) and/or the size of the ACL ruleset. In one embodiment, the order of the qualification patterns is adjusted to: (1) minimize the quantity of states per level in the Early portions of the state machine (where each "level" of a state machine comprises each state that is a same number of states from a start state of the state machine), and/or (2) position branches in the Later portions of the state machine as close as possible to the start state. In one embodiment, Early and Later portions of a state machine are determined based at least partly on the cache size. In one embodiment, the Early portions of the state machine comprise states that are cacheable, while the Later portions of the state machine comprise states that are not cacheable.

In certain embodiments, ACLs receive packets from fewer destinations than sources. Thus, in these embodiments, the destination-related fields of the qualification patterns may be positioned in an initial portion of the qualification pattern, such as in the exemplary order: protocol+DEST MAC+DEST IP+DEST PORT+SOURCE IP+SOURCE MAC+SOURCE PORT. By ordering the fields of the qualification pattern based on the types and/or sources of packets that pass through an ACL, the speed of the resultant state machine may be optimized as the most widely used branches of the state machine are marked as cacheable. In certain embodiments, the RegEx compiler 310 (FIG. 3) may be configured to analyze the use of fields in a particular ACLs qualification patterns in order to determine the optimal ordering of the fields prior to generating the regular expressions.

The RegEx to state machine compiler 320 (also referred to herein as the "state machine compiler 320") converts the regular expressions and match result codes from the RegEx compiler 310 into one or more state machines comprising a plurality of states having corresponding state transition instructions. For example, the regular expressions and match result codes for a single ACL may be combined into a single state machine having multiple terminal states corresponding with matches of the qualification patterns of the ACL 130. The state machine compiler 320 may generate the state machine at design time, such as when a network switch comprising the access control module 300 is assembled by an OEM, or dynamically as the ACL 130 is received and/or updated. In one embodiment, the state machine compiler 320 is configured to optimize the state machine to include the fewest state transition instructions that uniquely match the qualification patterns of the ACL 130. In the embodiment of FIG. 3, the state transition instructions generated by the state machine compiler 320 are stored in a state machine memory 342, which may comprise one or more memories (See FIG. 8, for example). In one embodiment, for each state of the state machine the state machine memory stores a state transition instruction comprising: a current state, an input that triggers a move to a next state, a next state, and an action associated with the next state. In other embodiments, the state transition instructions may comprise fewer or additional fields.

When a packet is received in the Ethernet packet stream 220, the packet's qualification content is extracted and compiled into a predetermined packet fingerprint. As noted above, in one embodiment, a packet fingerprint comprises information regarding each of the 7-tuple components of the packets, in a specified order. In other embodiments, the packet fingerprint comprises information regarding fewer or additional attributes of the packets. For example, in another embodiment, the packet fingerprint comprises information regarding the payload of the packets, in addition to information regarding one or more components of the packets 7-tuple.

Having generated a packet fingerprint, the a state machine engine 344 traverses the state machine stored in memory 342 using the bits of the packet fingerprint, until zero or more terminal states of the state machine are reached. When a terminal state is reached, the match result codes associated with the terminal states are passed to the result processing engine 330. In one embodiment, the match result codes are indicated in the state transition instructions of the terminal states. In one embodiment, the result processing engine 330 determines an action to be performed based on a selected highest priority match result code outputted from the state machine module 340. If the action associated with the highest priority match result code is to deny the packet from passing through the network switch, the result processing engine 330 may provide an indication to the network switch that the packet should be blocked. In another embodiment where the access control module 300 is implemented into an Ethernet switch, the result processing engine 330 may actually perform the packet blocking. In embodiments where the actions are more sophisticated than simply permitting or denying packets, the result processing engine 330 may initiate and/or perform such enhanced actions.

Figure 4:
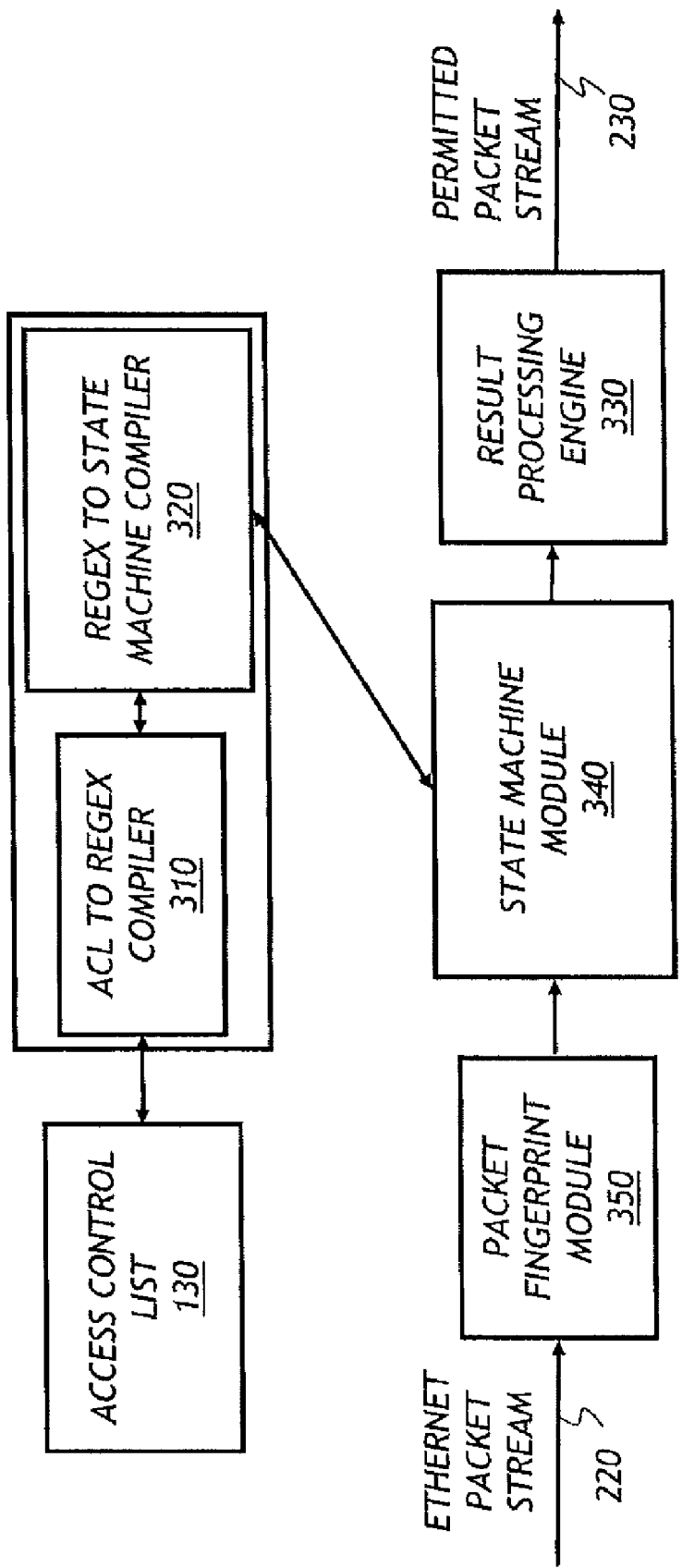
FIG. 4 is a block diagram of the modules of FIG. 3 in a functional relationship, showing the flow of data between the modules.

FIG. 4 is a block diagram of the modules of FIG. 3 in a functional relationship, showing the flow of data between the modules. In the embodiment of FIG. 4, the ACL 130, the RegEx compiler 310, and the state machine compiler 320 perform operations prior to receiving packets in the Ethernet packet stream 220 for which access control according to the access control list 130 is desired. More particularly, the RegEx compiler 310 compiles the qualification patterns of the access control list 130 into regular expressions and corresponding match result codes, and the state machine compiler 320 generates a state machine corresponding to the regular expressions and match result codes prior to filtering of packets. The ACL 130 may be user configured, generated by a Network Access Control (NAC) system, or developed in any other manner. In one embodiment, the ACL 130 indicates a method for determining a priority of rules, while in other embodiments the rule priority may be implied by the order of the rules in the ACL.

In the embodiment of FIG. 4, the state machine compiler 320 is in communication with the state machine module 340 and the state transition instructions generated by the state machine compiler 320 are stored in the state machine memory 342 of the state machine module 340. In certain embodiments, the state machine memory 342 comprises one or more memories, such as DRAMs, SRAMs, or other memories. For example, FIG. 8, described in further detail below, illustrates one embodiment of the state machine memory 342 that comprises three memories for storing different portions of the state transition instructions in a manner that increases the speed of processing the incoming packets while minimizing the size of faster, more expensive memory.

Figure 8:
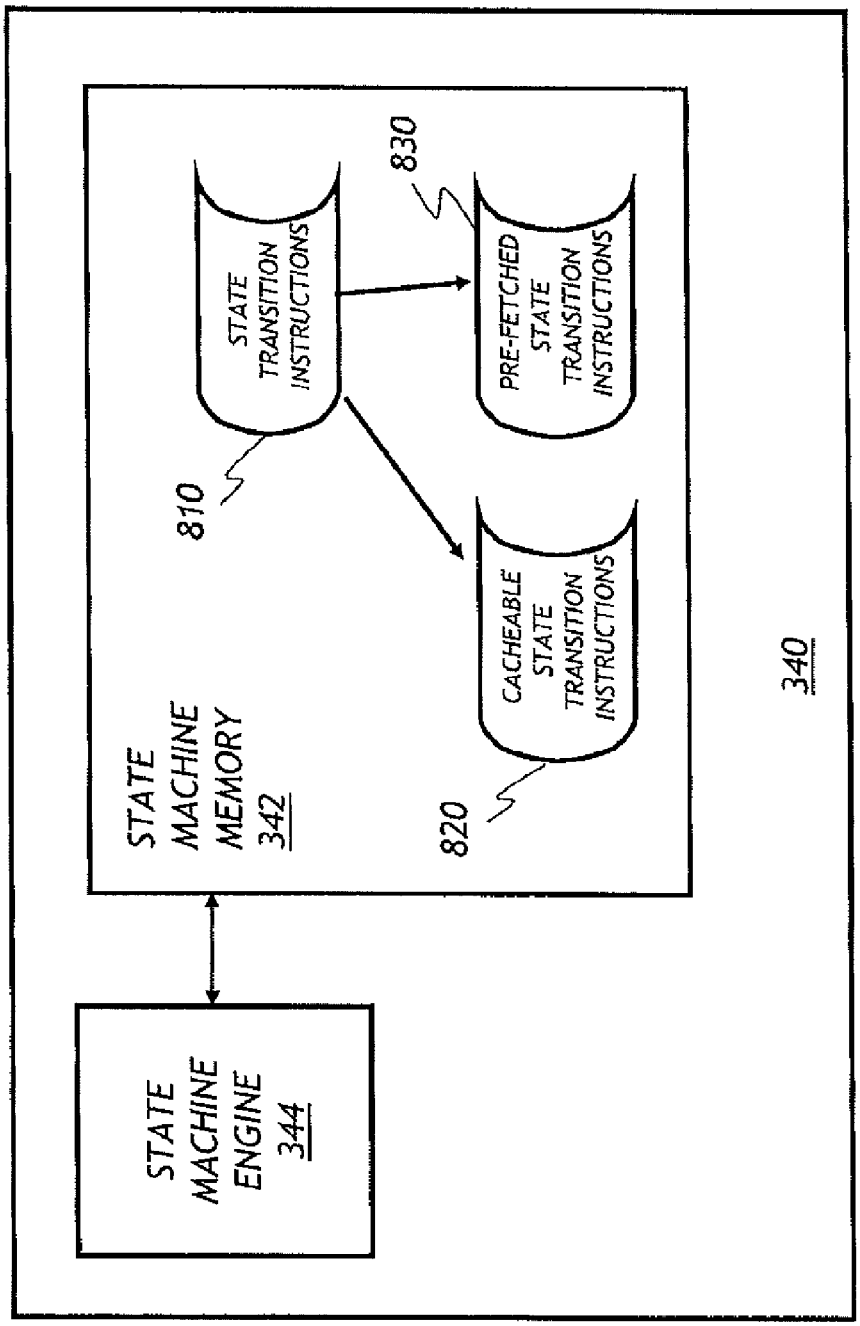
FIG. 8 is a block diagram illustrating one embodiment of the state machine module of FIG. 4.

With the state transition instructions stored in the state machine memory 342, the access control module 300 is ready to control access of packets according to the qualification patterns and actions of the ACL 130. As shown in FIG. 4, the Ethernet packet stream 220 is received by the packet fingerprint module 350, which is configured to access portions of the packet in order to compile a packet fingerprint. As noted above, in one embodiment a packet fingerprint comprises information regarding each of the 7-tuple components of packets, such as illustrated in FIG. 3A. Depending on the embodiment, the packet fingerprint module 350 may include information regarding only a portion of the 7-tuple components or may also include information regarding the packet payload, or any other component of the packets. The packet fingerprint is transmitted to the state machine module 340, which traverses the state transition instructions stored in the state machine memory 342 using the bits of the packet fingerprint. In one embodiment, the state transition instructions are organized in the memory 342 so that commonly accessed portions of the state machine are stored in a fast memory, such as a buffer, so that the speed of traversing those commonly accessed portions may be increased. FIG. 8, described in further detail below, illustrates one embodiment of the memory 342 comprising multiple memory types.

In the embodiment of FIG. 4, the state machine module 340 outputs to the result processing engine 330 a match result code associated with each terminal state that is reached for a provided packet fingerprint. The result processing engine 330 determines, based at least partly on the match result codes, an action to perform on the corresponding data packet. Thus, depending on the respective terminal states reached for packets of the packet stream 220, certain of the packets may not be included in the permitted packet stream 230, while other packets will be included in the permitted packet stream 230. In one embodiment, the permitted packet stream includes packets destined for multiple computing devices, such as the various computing devices 140 of FIG. 1.

Figure 5:
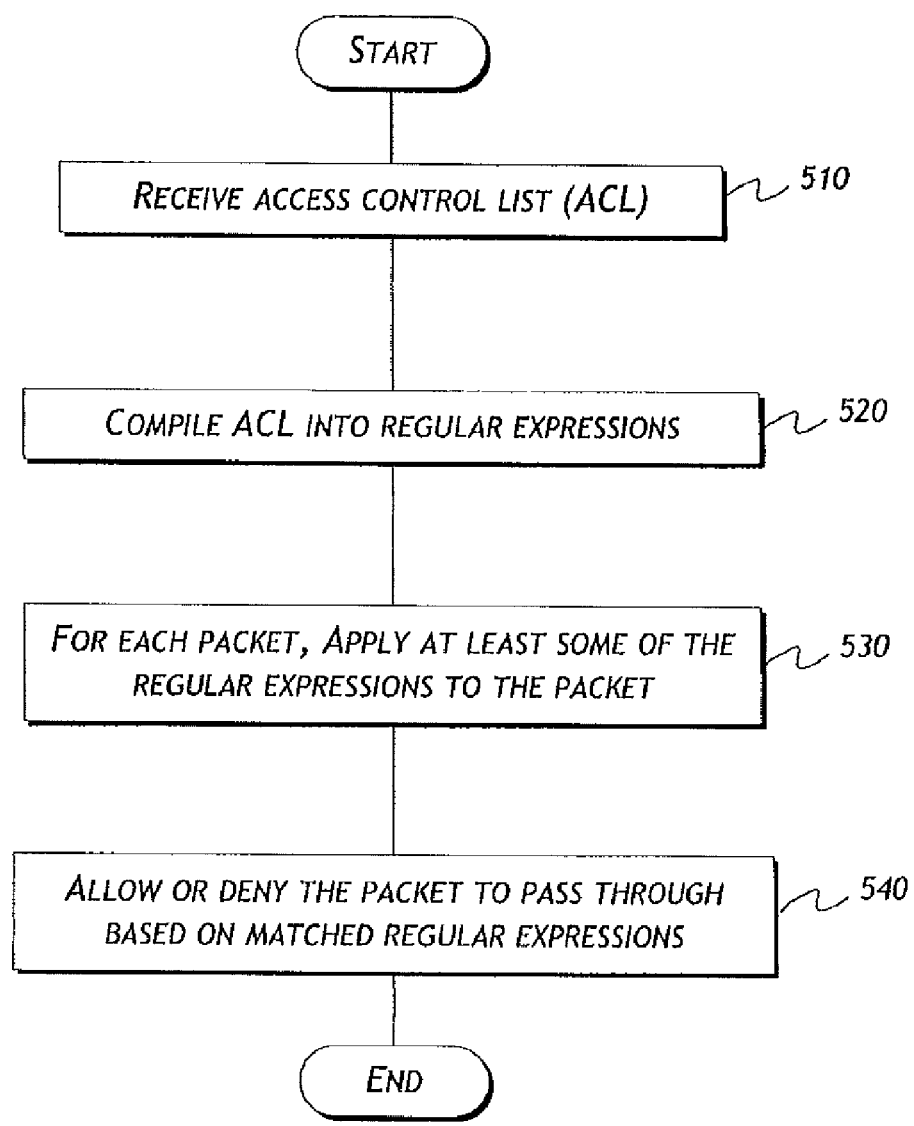
FIG. 5 is a flowchart illustrating one embodiment of a method of monitoring packet flow through a switch.

FIG. 5 is a flowchart illustrating one embodiment of a method of monitoring packet flow through a switch. Beginning in a block 510, an access control list is received, such as by the access control module 300 (FIG. 3). In one embodiment, priority preferences for rules of the ACL are also received. In one embodiment, a standard ACL for corporate intranets, for example, may be received. In other embodiments, each switch may have a custom ACL, comprising unique qualification patterns and/or actions. In other embodiments, an ACL may comprise a combination of standard ACL's, as well as custom qualification patterns and actions. In one embodiment, the ACL is updated by a network administrator, for example, based on changing access control needs. In other embodiment, the access control list may be updated by any service that maintains an updated list of security threats.

Continuing to a block 520, the ACL is compiled into one or more regular expressions. In one embodiment, the ACL is compiled into regular expressions by the RegEx compiler 310 of FIGS. 3 and 4. In other embodiments, other components may convert the qualification patterns and actions of the ACL into corresponding regular expressions.

Moving to a block 530, for each packet received in a packet stream, at least some of the regular expressions are applied to the packet. For example, a first regular expression may define a pattern comprising a source IP address and a destination IP address, while a second regular expression may define a pattern comprising a source MAC address and destination TCP address. In one embodiment, the regular expressions are evaluated based on qualification content contained in the packet headers of the packets, and/or other portions of packets. In one embodiment, the regular expressions are evaluated using one or more state machines, such as a state machine that is compiled by the state machine compiler 320 of FIGS. 3 and 4. In other embodiments, the regular expressions may be evaluated in other matters.

Next, in block 540, packets are allowed or denied passage through the access control module based on actions associated with one or more matched regular expressions. In one embodiment, regular expressions are ordered in a ranked manner, such that the highest priority regular expression (corresponding to the highest priority ACL rule) is evaluated first, while a least important regular expression is evaluated last. In this embodiment, the first regular expression that is matched may dictate the action performed on the corresponding packet, if any. Thus, if the first regular expression match is associated with a permit action, the packet would be allowed to pass through the access control module. In another embodiment, such as where the regular expressions are evaluated concurrently in a state machine, multiple terminal states may be reached for a single packet. In this embodiment, the first regular expression matched may not necessarily represent the highest priority regular expression, but instead may represent the regular expression having a shorter branch through the state machine. Thus, in one embodiment the regular expressions are associated with rankings that are accessed by the result processing engine 330 in order to determine which of multiple matched regular expressions is the most important regular expression and, thus, which action should be performed on the packet. In one embodiment, match result codes that are output by the state machine module 340 upon reaching a terminal state are used by the result processing engine 330 to determine a highest priority regular expression and, thus, to determine an action associated with that highest priority regular expression.

Figure 6:
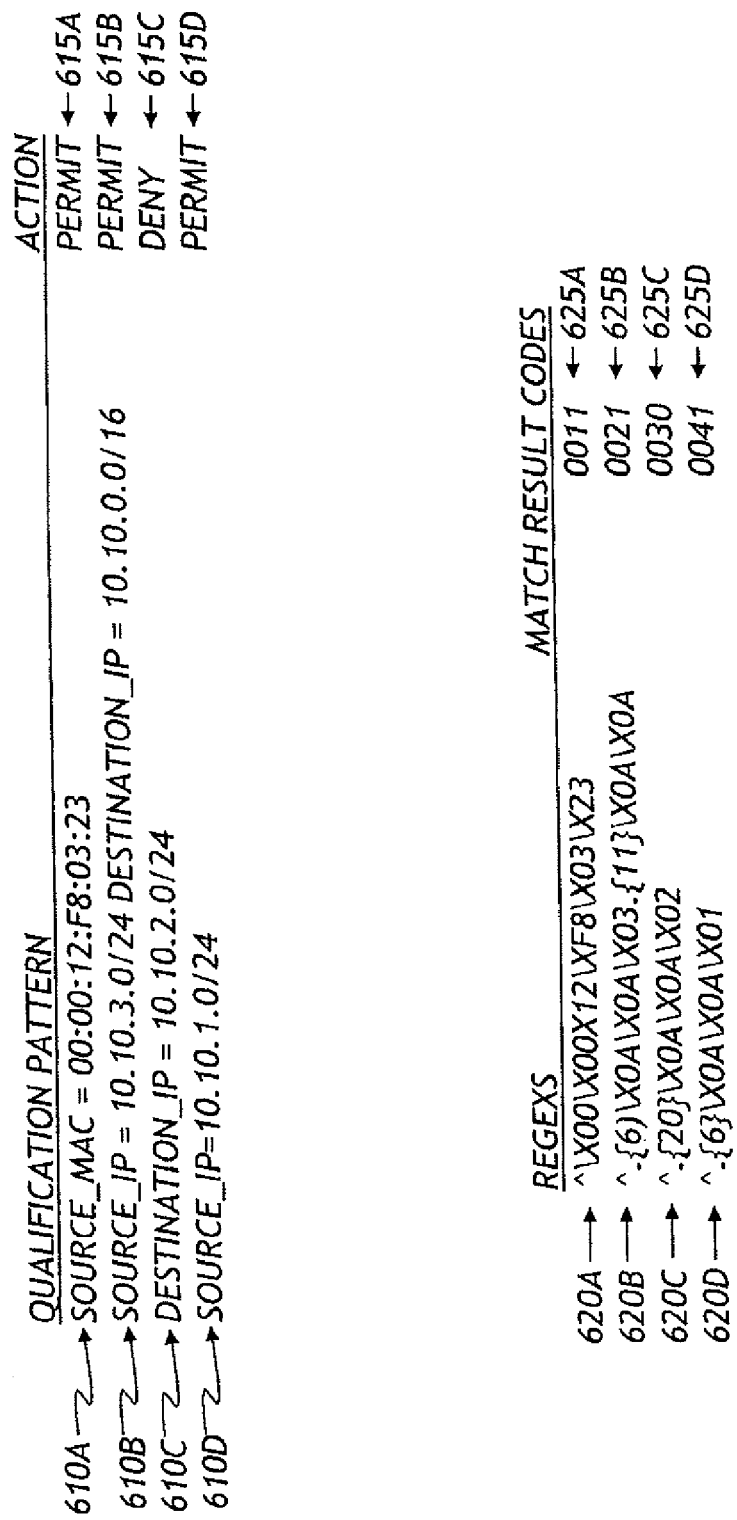
FIG. 6 illustrates exemplary qualification patterns and actions of an ACL and the corresponding regular expressions and match result codes.

FIG. 6 illustrates exemplary qualification patterns 610 and actions 615 of an ACL, as well as the corresponding regular expressions 620 and match result codes 625. As illustrated in FIG. 6, the access control list comprises four qualification patterns 610A, 610B, 610C, and 610D associated with respective actions 615A, 615B, 615C, and 615D. Exemplary qualification pattern 610A considers only the source MAC address of incoming packets, while exemplary qualification pattern 610B considers both the source IP address and the destination IP address of packets. In this embodiment, if the source MAC address of a packet fingerprint matches the qualification pattern 610A, the packet is to be permitted passage through the access control module. Similarly, if the packet fingerprint matches the indicated source IP address and destination IP address of qualification pattern 610B, the packet is to be permitted passage through the access control module. In other embodiments, access control lists may comprise hundreds, thousands, or even millions of qualification patterns and associated actions.

FIG. 6 also illustrates the regular expressions 620A-620D and match result codes 625A-625D that correspond with respective qualification patterns 610A-610D and actions 615A-615D. In the embodiment of FIG. 6, each of the regular expressions 620 is associated with a match result code 625, which indicates that the respective regular expression has been matched and, in some embodiments, is usable to determine relative priorities of match result codes 625. For example, in the embodiment of FIG. 6, if regular expression 620A is matched by a packet fingerprint, the match result code of '0011' is transmitted from the state machine module 340 to the result processing engine 330. In one embodiment, the match result codes are numerically ranked, such that the lowest numerical match result code, e.g., '0001', represents the highest priority regular expression. In this embodiment, if multiple regular expressions are matched by a particular packet fingerprint, the action associated with the numerically lowest match result code, indicating the highest priority regular expression, is performed.

FIG. 7 illustrates exemplary code 710 that may be executed by the result processing logic 330 (FIGS. 3 and 4) in order to select a highest priority matched rule in response to receiving one or more match result codes from the state machine module 340. FIG. 7 further illustrates packet fingerprints 720A, 720B associated with two packets, and the associated state machine module 340 output that results from application of the regular expressions 620 of FIG. 6. As illustrated in FIG. 7, the packet fingerprint 720A results in two state machine outputs, a first match result code of '0021' indicating a match of regular expression 620A (and corresponding qualification pattern 610A) and a second match result code of '0030' indicating a match of regular expression 620C (and corresponding qualification patter 610C). In one embodiment, depending on the state machine module 340 configuration, the state machine engine 344 outputs match results codes in the order that their corresponding terminal states are reached. Thus, the match result codes may be output in any order, such as '0030' then '0021', or in the reverse order.

As noted above, if the state machine module 340 outputs multiple match result codes, the highest priority rule may be selected based on the numerical relationship of the match result codes, such as where the lowest match result code indicates a highest priority results. In other embodiments, other match result codes may be received from the state machine module 340, and other methods for determining a highest priority rule may be implemented. In the exemplary code 710, the result processing logic 330 initially sets a default action to permit an incoming packet. This default action is then changed as one or more match result codes, corresponding with matched regular expressions, are received from the state machine module 340. In the embodiment of FIG. 7, the default action is only updated with actions associated with match result codes having lower numerical values than a match result code associated with a currently selected action. Accordingly, with respect to packet fingerprint 720A, the order of receiving the match result codes '0021' and '0030' does not affect the action that is selected by the result processing engine 330. For example, if the match result code '0021' is received first by the result processing engine 330, the selected action will be updated with the corresponding permit action. When the state machine output '0030' is later received, the selected action will not be updated, because the currently selected match result code (e.g., '0021') is numerically lower than '0030'. Accordingly, the action associated with the match result code '0021' is performed, permitting the packet to pass through the switch. Similarly, if the match result code '0030' is received first by the result processing engine 330, the selected action will be updated with the corresponding deny action. However, in an advantageous embodiment, the deny action is not executed until all possible state machine outputs for a particular packet fingerprint are received by the result processing engine 330. Thus, when the match result code '0021' is later received, the selected action is updated with the corresponding permit action, due to the lower numerical value of the match result code '0021', and the packet is permitted to pass through the switch.

FIG. 8 is a block diagram illustrating one embodiment of the state machine module 340 of FIG. 4. As illustrated in FIG. 8, the exemplary state machine module 340 comprises a state machine engine 344 and the state machine memory 342, which comprises three memories, including a DRAM 810, a SRAM 820, and a buffer 830. In this embodiment, the state machine engine 344 controls the operation of the state machine module 340, such as by analyzing portions of the packet fingerprint in order to traverse the state transition instructions stored in the memory 342. While certain embodiments may store and access state transition instructions from a single memory, such as a single DRAM, use of a minimum amount of low latency memory, such as SRAM memory, may advantageously increase the speed of the state machine module 340, while limiting the size of this more expensive memory. More particularly, ACLs may result in thousands of state transition instructions (with 10s or 100s of millions of bytes required for state instruction storage) and memory inexpensive enough to hold all of these state transition instructions (such as SDRAM) has a high read access latency, creating an ACL processing latency intolerable to Ethernet switching. Conversely, more expensive RAM technology (like SSRAM or TCAM) can meet the latency requirements, but cannot hold all of the ACLs desired. Accordingly, as described with regard to FIG. 8, portions of the state transition instructions are copied to one or more faster memories (also referred to herein as caches or cache memories) in order to achieve a higher performance state machine with minimal high speed memory requirements.

In the embodiment of FIG. 8, the state transition instructions of the generated state machine are stored in the DRAM 810 as the state transition instructions are received from the state machine compiler 320. However, due to the relatively high read access latency and speed of DRAM memories, portions of the state transition instructions are advantageously copied to one or more faster memories for evaluation of incoming packet fingerprints. In the embodiment of FIG. 8, the SRAM 820 comprises state transition instructions that are determined to be cacheable, such as by the state machine compiler 320, for example. For example, the state machine compiler 320 may flag those state machine instructions associated with state transitions that are most likely to be repeatedly traversed by multiple packet fingerprints. In one embodiment, the buffer 830 comprises state transition instructions that are prefetched based on a current branch of the state machine that is being followed by a particular packet fingerprint. Use of the SRAM 820 and buffer 830 will be described in further detail with respect to FIG. 9, below. In other embodiments, the memory 342 may comprises fewer or additional memories. For example, in another embodiment, the memory 342 does not include a buffer 830, but instead stores pre-fetched state transition instructions in the SRAM 820, as well as the cached state transition instructions.

Figure 9:
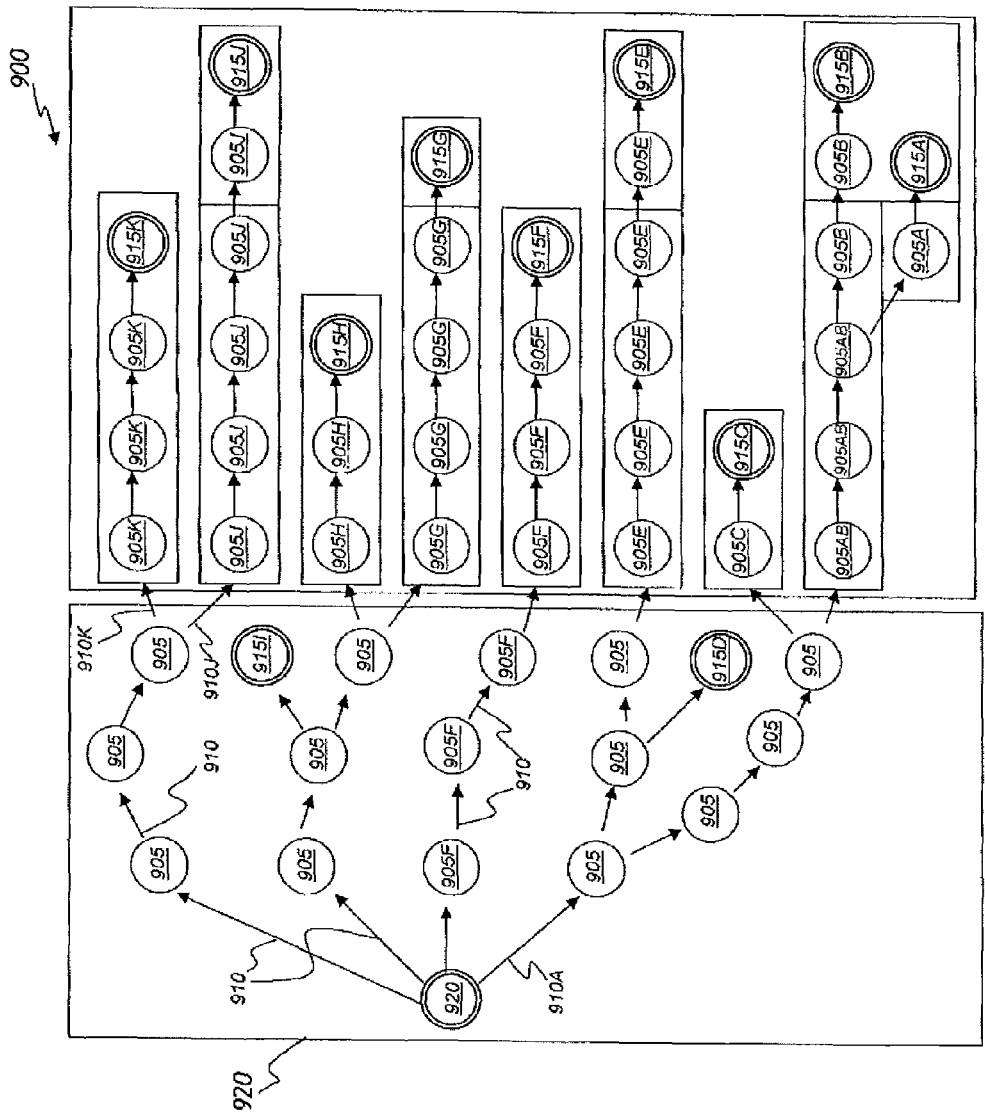
FIG. 9 illustrates one embodiment of a state machine having portions selectively stored in multiple memory devices.

FIG. 9 illustrates one embodiment of a state machine 900 stored in the DRAM 810, wherein a portion of the state machine is copied to the SRAM 820, and other portions of the state machine are selectively prefetched into the buffer 830 as the state machine is traversed by respective packet fingerprints. In the embodiment of FIG. 9, each of the circles represent states 905 of the state machine, and the arrows 910 between the states represent instructions associated with a transition from one state to another. In one embodiment, the state transition instructions associated with the arrows of FIG. 9 are stored in the state machine memory 342. In one embodiment, the state transition instructions each include a current state, a next state, and a condition that needs to be fulfilled to enable the respective transition from a current state to a next state, such as receiving a particular bit of the packet fingerprint. The state transitions instruction may further comprises actions, which may contain a match result code that is to be output from the state machine module 340.

In the embodiment of FIG. 9, the double line circles represent a start state 920 and terminal states 915 of the state machine, where the terminal states 915 indicate that a regular expression corresponding with a qualification pattern has been matched by the packet fingerprint. In the embodiment of FIG. 9, the terminal states are associated with respective match result codes that are transmitted from the state machine module 340. For example, in one embodiment the match result code data associated with terminal states 915 is the corresponding numerical match result codes that are generated by the state machine compiler 320, such as the exemplary outputs '0011', '0021', '0030' and '0041' that are associated with regular expressions 620A-620D of FIG. 6.

As illustrated in the exemplary state machine 900, the start state 920 comprises multiple branches to respective states 905, and additional branches to multiple states occur subsequently in many of the state machine branches. For each complete branch of the state machine, however, the terminating state 915 and zero or more states 905 are unique to a single branch, and to a particular regular expression and qualification pattern. For example, the branch that terminates with terminal state 915C includes one state 905C and the terminal state 915C that are unique to a single branch of the state machine 900. Similarly, the branch that terminates with terminal state 915E comprises five states 905E and the terminal state 915E that are unique to that specific branch, and also to a specific regular expression and corresponding ACL rule. The states that are unique to a single branch of the state machine are not likely to be accessed as frequently as states 905 that are traversed with respect to multiple branches of the state machine 900. For example, state transition 910A indicates a transition to a series of branches having five possible terminal states 915A, 915B, 915C, 915D, and 915E. Thus, the states 905 immediately after the transition 910A are likely to be accessed more frequently than states that are unique to a particular branch of the state machine, such as states 905A, 905B, 905C, 905E, 905F, 905G, 905H, 905J, 905K and the terminal states 915. More generally, the states near a head 920 of the state machine 900 are likely to be traversed more frequently than states near a tail 930 of the state machine.

Accordingly, in one embodiment a predetermined number of state transition instructions in each branch of the state machine are cached to a faster memory, such as the SRAM 820 of FIG. 8, so that these more frequently used state transition instructions are readily available in the faster SRAM 820. For example, in the embodiment of FIG. 9, the first four state transitions instructions of each state machine branch, starting immediately after the start state 920, are designated as cacheable by the state machine compiler 320. Thus, when the state transition instructions are stored in the state machine module 340, these cacheable states are stored in the faster SRAM 820, rather than, or in addition to, storage of these state transition instructions in the DRAM 810. In other embodiments, other types of memory may be used to store the state machine 900, rather than the DRAM 810, and cacheable portions of the state machine, rather than SRAM 820.

In addition to storage of commonly accessed state transition instructions of the state machine 900 in the faster SRAM 820, the speed of the state machine may be further improved by prefetching state transition instructions associated with states in the tail 930 of the state machine 900, for example, where prefetching occurs as particular branches of the state machine 900 become more probable or certain to be traversed. In one embodiment, state transitions 910 that lead to states that are specific to no more than a predetermined number of branches, such as 1 branch, for example, comprise indications that the remaining possible branch(es) are to be pre-fetched into the buffer 830. For example, when state transition 910K is reached, only a single branch, associated with a single regular expression, remains to be traversed. Accordingly, either the packet fingerprint will result in a terminating at the terminal state 915K, or the packet fingerprint will result in terminating prior to terminal state 915K. In either case, only states 905K and 915K are possible for traversal after state transition 910K. Accordingly, in one embodiment the transition 910K is associated with instructions indicating that state transition instructions for states 905K and 915K should be copied from DRAM 810 into a faster buffer 830 so that further transitions along that branch of the state machine may be completed more quickly than if the state transition instructions remain in the DRAM 810. Accordingly, upon reaching transition 910K, the state machine engine 344 may initiate prefetching of state transition instructions 905K and 915K. Similarly, if state transition 910J is reached, the state machine engine 344 may initiate prefetching of states 905J and 915J, in response to an instruction, such as a pre-fetch flag, included in the action field of the state transition instruction for the state 905 associated with the transition 910J. In other embodiments, state transition instructions may be prefetched when there are less than 2, 3, 4, 5 or more remaining possible terminal states downstream in a particular branch. In another embodiment, as many most probable next states as will fit in the buffer 830 are prefetched whenever a transition is made out of the SRAM cache 820 and/or whenever a transition is made out of the buffer 830. In this embodiment, the buffer 830 is filled with the most probable next states at times when state machine operation is slowing due to transitioning from state transition instructions in a faster memory to instructions stored in a slower memory.

In one embodiment, the speed at which state transition instructions may be retrieved from DRAM 810 is increased by storing adjacent state transition instructions in sequential memory of the DRAM 810. As those of skill in the art will recognize, certain memory devices support burst reads, wherein multiple sequential memory addresses are read from the memory in response to a single read request. For example, using burst mode in DDR2 memory, the content of four or eight memory addresses is returned in response to a read request for a single address. Thus, if the DDR2 memory is sufficiently wide to contain a state transition instruction at each address, four state transition instructions may be read from the memory in a single read request. By aligning adjacent states of the state machine in sequential memory locations, rather than allowing sequential state transition instructions to be stored in fragmented memory, the states may be more quickly read from the DRAM 810. For example, when the state transition instruction 910K is reached, four total states (three states 905K and a terminal state 915K) remain in the selected branch. Accordingly, in an embodiment where DRAM 810 comprises DDR2 memory, or other memory that supports burst reads of four or more memory addresses, state transition instruction associated with all four remaining states may be retrieved from DRAM 810 in a single memory access cycle, thereby reducing the time required to prefetch those state transition instruction instructions. With the state transition instructions prefetched in a faster buffer 830, the states may be more quickly traversed than if they remained in the DRAM 810. In other embodiments, memory devices may have different bursting modes, such as bursting 2, 6, 8, 16, or 32 memory addresses in response to a single read request.

A variety of techniques can be used to enforce the caching and/or prefetching strategy determined by the state machine compiler 320, including, for example, mapping state transition instructions into cacheable and non-cacheable address spaces of the DRAM 810, including caching indicators in the state transition instructions themselves indicating whether an instruction should be cached (as described above, for example), and/or including prefetching indicators indicating which state transition instruction should be prefetched and when those instructions should be prefetched. Other techniques may also be used.

Figure 10:
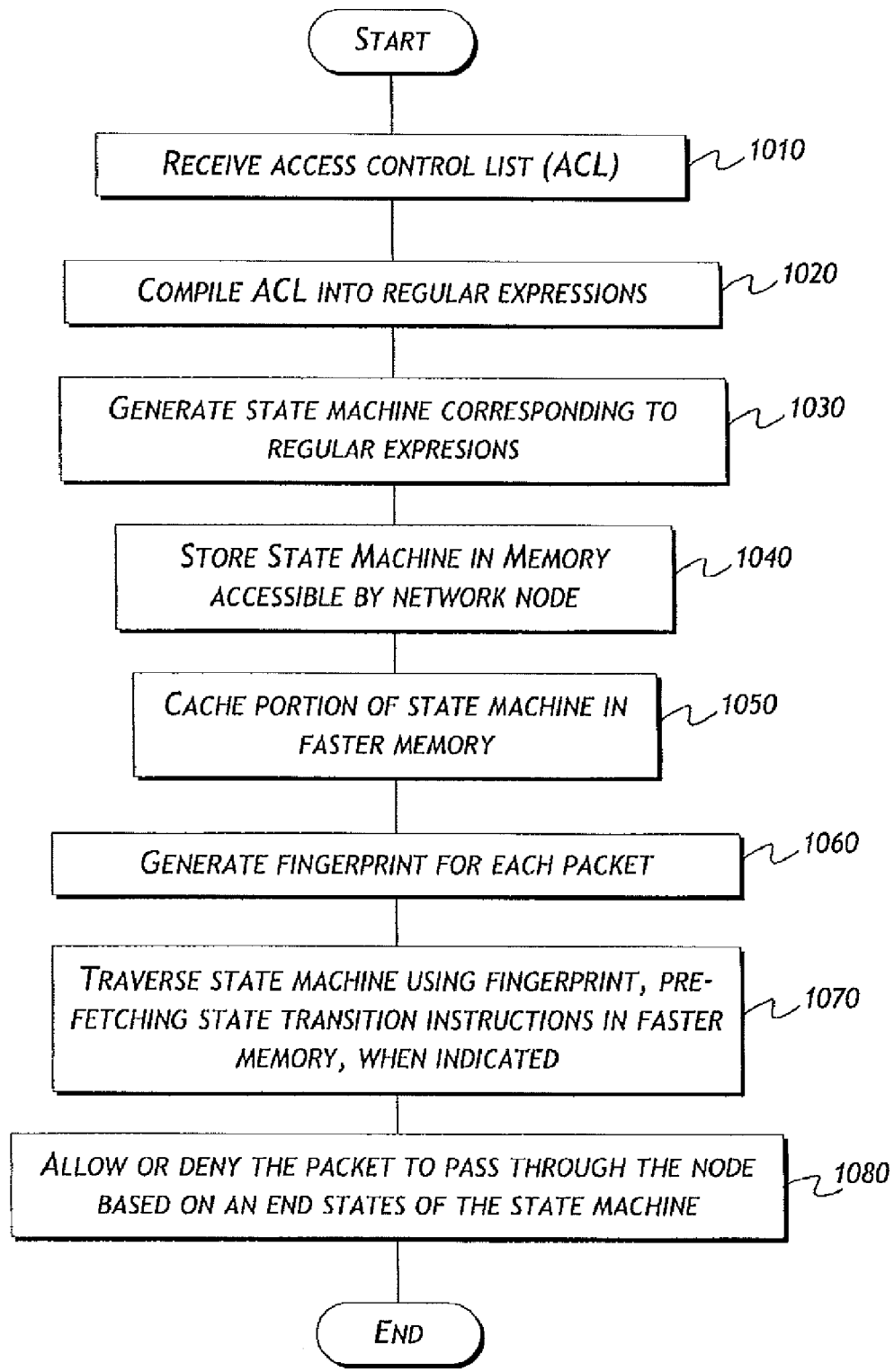
FIG. 10 is a flowchart illustrating one embodiment of a method of controlling flow of packets according to an ACL comprising multiple qualification patterns and associated actions.

FIG. 10 is a flowchart illustrating one embodiment of a method of controlling flow of packets according to rules of an ACL, wherein each of the rules comprises a qualification pattern and an associated action. Advantageously, the method of FIG. 10 generates regular expressions associated with the qualification patterns and actions of the ACL that may be more efficiently evaluated with respect to packets in a packet stream.

Beginning in block 1010, an access control list is received, such as by the RegEx compiler 310 of FIG. 3. As noted above, the ACL may come from one of many sources, and may be updated on a periodic basis.

Continuing to block 1020, the ACL is compiled into a series of regular expressions. For example, in one embodiment the RegEx compiler 310 (FIGS. 3-4) converts each of the qualification patterns and associated actions into a corresponding regular expression and match result code, where the regular expressions match packet fingerprints that satisfy the respective qualification patterns. In certain embodiments, more than one qualification pattern may be combined into a single regular expression.

Continuing to block 1030, a state machine corresponding to the generated regular expressions is generated. In one embodiment, the state machine compiler 320 (FIGS. 3 and 4) accesses the regular expressions and match result codes in order to generate a corresponding state machine comprising multiple state transition instructions. In one embodiment, each of the terminal states of the state machine correspond with matching of one or more qualification patterns in the original ACL.

Next, in block 1040 the state transition instructions are stored in one or more memories that are accessible by a network node for which packet flow is to be monitored. For example, in one embodiment the network node comprises an Ethernet switch that is in communication with a plurality of computing devices. In other embodiments, the network node may be located at a server, router, or any other location where packets are transmitted. In one embodiment, the analysis of packets by the access control module 300, for example, is performed in a non-intrusive manner, such that flow of packets through the network node is not affected, except for those packets that are denied passage based on actions associated with matching qualification patterns. As noted above with respect to FIG. 8, the state machine may be stored in one or multiple memories in order to increase the speed at which the states of the state machine are cached and/or prefetched for traversal by the state machine engine 344.

Continuing to block 1050, a portion of the state transition instructions are cached in faster memory, such as the SRAM 820. In one embodiment, the state transition instructions that are cached are those associated with states that are likely to be traversed most frequently as packet fingerprints are analyzed. As noted above, in one embodiment state transition instructions associated with a predetermined number of states of each branch of the state machine are indicated as cacheable by the state machine compiler 320, and are accordingly stored in the SRAM 820. In other embodiments, the number of state transition instructions that are cached in each branch of the state machine may vary depending on one or multiple factors. For example, in one embodiment a predetermined number of state transition instructions for each branch are preliminarily marked as cacheable by the state machine compiler 320, but certain branches having one or more of the states marked for caching that are in a linear branch of the state machine may be unmarked as cacheable. In the embodiment of FIG. 9, for example, three states 905F are included in the head 920 of the state machine 900. These states 905F are only part of a linear branch of the state machine 900 that terminates at terminal state 915F. Accordingly, in one embodiment the preliminary cacheability marking of these states may be removed in order to preserve the cacheable memory for states that are used by multiple branches of the state machine 900. For example, states 905AB in tail 930 of the state machine 900 are common to two branches of the state machine, in particular, branches terminating at terminal states 915A and 915B. Thus, in one embodiment one or more of these overlapping states 905AB are also marked as cacheable by the state machine compiler 320. Accordingly, in one embodiment a predetermined number of states (e.g., the head portion 920) are initially marked for caching, the caching mark is removed from certain states in linear branches (e.g., states 905F in the head portion 920), and/or additional states in overlapping branches (e.g., states 905AB) are marked for caching. In other embodiments, the caching indicators may be determined in other matters, such as based on a size of the state machine compared to a size of available SRAM.

Continuing to a block 1060, a packet in a packet stream is received and a packet fingerprint is generated for the packet. As noted above, in one embodiment the packet fingerprint comprises indicators of each of the 7-tuple components of the packet, as shown in FIG. 3A, for example. In other embodiments, the packet fingerprint comprises fewer or additional pieces of information regarding the received packet. For example, in one embodiment the packet fingerprint comprises information regarding a payload of the packet, such as a predetermined number of bits of the packet payload. In this embodiment, the qualification patterns of the ACL may include rules that match specific content within the packet payload, thereby providing additional granularity for controlling access of packets. In one embodiment, for example, qualification patterns may be generated to detect virus patterns in the payload of a packet. In one embodiment, the packet fingerprint for each packet is in the same known format, such as the format illustrated in FIG. 3A, for example, so that the state machine may accurately analyze relevant portions of the packet fingerprint.

Continuing to a block 1070, the state transition instructions stored in the one or more memories is traversed using bits of the packet fingerprint, and zero or more terminal states are reached. As described above with reference to FIG. 7, for example, the packet fingerprint 720 reaches two terminal states of a state machine corresponding with regular expressions 620 (FIG. 6), which respectively outputs match result codes '0021' and '0030'. Depending on the qualification patterns and the packet qualification content, some packet fingerprints may not reach any terminal states of the state machine. As the state machine is traversed based on the packet fingerprint, certain state transition instructions of the state machine, such as those in the tail 930 of state machine 900 (FIG. 9), may be prefetched and stored in a faster memory, such as buffer 830, in order to accelerate evaluation of the packet fingerprint.

In a block 1080, the result processing engine 330, for example, determines an action to be performed on the packet associated with the packet fingerprint. In one embodiment, if zero terminal states of the state machine were reached, the packet is allowed to pass through the network node. In other embodiments, the default is to deny all packets that failed to match any qualification patterns in the ACL. In an embodiment where multiple terminal states were reached by a packet fingerprint, the result processing engine 330 determines which of the corresponding actions should be executed. For example, with respect to packet fingerprint 72DA, the result processing engine determines that the permit action associated with match result code '0021' should be executed, rather than the deny action associated with match result code '0030', due to the lower numerical value of match result code '0021'. In other embodiments, other methods may be performed in order to determine which of multiple actions should be performed based on respective match results codes. In one embodiment, if multiple match result codes are each associated with a common action, such as accept or deny, ranking of the match result codes is bypassed and the common action is executed. In one embodiment, permitting the packet to flow through the network node comprises taking no action. In other embodiments, permitting flow through the network node requires an affirmative command to the Ethernet switch, for example, that the packet should be allowed to pass.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of storing a state machine, the method comprising:
   storing a state machine in a memory, the state machine comprising a plurality of states and transitions therebetween, the state machine comprising a plurality of branches, each having a terminal state, that are associated with the matches of an input string to respective regular expressions;
   selecting a predetermined number of states in each branch of the state machine for storage in a cache memory that has faster access and read times than the memory;
   before receiving packets in a packet stream, selecting one or more additional states of at least a first branch of the state machine in response to determining that the first branch comprises unselected states that are associated with each of a plurality of branches;
   before receiving packets in the packet stream, deselecting one or more states of at least a second branch of the state machine in response to determining that the second branch comprises selected states that are only associated with the second branch;
   before receiving packets in the packet stream, storing the selected states of the state machine in the cache memory;
   in response to accessing a state of at least a third branch of the state machine, determining a number of third branch terminal states associated with the third branch; and
   if the number of third branch terminal states is less than a predetermined threshold, prefetching state transition instructions associated with each of the third branch terminal states for storage in a buffer memory.

2. The method of claim 1, further comprising:
   in response to accessing a last cached state of a fourth branch of the state machine, storing one or more additional states of the fourth branch in the buffer memory.

3. The method of claim 1, wherein state transition instructions associated with two or more states are retrieved from the memory in a single read cycle.

4. A computerized system for monitoring packet that pass through a network node, the system comprising:
   a memory storing a state machine, the state machine comprising a plurality of states and transitions therebetween, the state machine comprising a plurality of branches, each having a terminal state, that are associated with matches of an input string to respective regular expressions, and the state machine configured to:
   determine, in response to accessing a state of a branch, a number of terminal states corresponding to the branch;
   if the number of terminal states corresponding to the branch is less than a predetermined threshold, prefetch state transition instructions associated with each of the terminal states corresponding to the branch for storage in a buffer memory;
   select a subset of the plurality of states that are likely to be most frequently traversed by packets received by the network node;
   select, before receiving packets in a data stream, one or more additional states of at least a first branch of the state machine in response to determining that the first branch comprises unselected states that are associated with each of a plurality of branches; and
   deselect, before receiving packets in the packet stream, one or more states of at least a second branch of the state machine in response to determining that the second branch comprises selected states that are only associated with the second branch.

5. The computerized system of claim 4, wherein the state machine is configured to select only certain states for caching in cache memory having access and read times that are faster than the memory.

6. The computerized system of claim 4, wherein a predetermined number of states of each branch of the state machine are selected for caching.

7. The computerized system of claim 4, wherein a respective state is selected for caching if at least a predetermined number of branches each comprise the respective state.

* * * * *